(12) United States Patent
Ohba et al.

(10) Patent No.: US 11,759,774 B2
(45) Date of Patent: Sep. 19, 2023

(54) PURIFICATION PROCESS FOR HYDROPHILIC ORGANIC SOLVENT

(71) Applicant: Dow Global Technologies LLC, Midland, MI (US)

(72) Inventors: Kaoru Ohba, Tokyo (JP); Kenji Takano, Niigata (JP); Masonori Iida, Tokyo (JP); Shinnosuke Abe, Tokyo (JP); Takashi Masudo, Natori (JP); Osamu Kishizaki, Tokyo (JP); Ryo Ishibashi, Tokyo (JP); Yusuke Yamashita, Tokyo (JP)

(73) Assignee: Dow Global Technologies LLC, Midland, MI (US)

( * ) Notice: Subject to any disclaimer, the term of this patent is extended or adjusted under 35 U.S.C. 154(b) by 126 days.

(21) Appl. No.: 16/067,031

(22) PCT Filed: Dec. 16, 2016

(86) PCT No.: PCT/US2016/067172
§ 371 (c)(1),
(2) Date: Jun. 28, 2018

(87) PCT Pub. No.: WO2017/116755
PCT Pub. Date: Jul. 6, 2017

(65) Prior Publication Data
US 2019/0009266 A1    Jan. 10, 2019

(30) Foreign Application Priority Data
Dec. 28, 2015 (JP) .................................. 2015-256337

(51) Int. Cl.
*B01J 47/04* (2006.01)
*B01J 39/05* (2017.01)
*B01J 41/05* (2017.01)
*B01D 15/36* (2006.01)
*B01J 39/18* (2017.01)
*B01J 41/12* (2017.01)
*C07C 41/36* (2006.01)

(52) U.S. Cl.
CPC ............ *B01J 47/04* (2013.01); *B01D 15/362* (2013.01); *B01D 15/363* (2013.01); *B01J 39/05* (2017.01); *B01J 39/18* (2013.01); *B01J 41/05* (2017.01); *B01J 41/12* (2013.01); *C07C 41/36* (2013.01)

(58) Field of Classification Search
None
See application file for complete search history.

(56) References Cited

U.S. PATENT DOCUMENTS

| | | | | |
|---|---|---|---|---|
| 5,192,446 A | * | 3/1993 | Salem | B01J 39/05 210/686 |
| 5,446,125 A | * | 8/1995 | Honda | C08F 6/06 430/190 |
| 5,500,127 A | * | 3/1996 | Carey | B01J 39/07 210/685 |
| 5,518,628 A | | 5/1996 | Carey | |
| 6,054,109 A | * | 4/2000 | Saito | B01D 15/00 423/584 |
| 6,123,850 A | | 9/2000 | Commarieu et al. | |
| 6,200,479 B1 | * | 3/2001 | Zampini | C08G 8/10 210/683 |
| 7,329,354 B2 | | 2/2008 | Mullee | |
| 10,913,058 B2 | * | 2/2021 | Ohba | B01J 41/12 |
| 2003/0047507 A1 | * | 3/2003 | Hou | B01J 39/18 210/502.1 |
| 2003/0138710 A1 | | 7/2003 | Park et al. | |
| 2006/0219259 A1 | * | 10/2006 | Oh | C23G 1/10 134/2 |
| 2018/0273465 A1 | * | 9/2018 | Muneyasu | B01J 39/26 |
| 2019/0009267 A1 | * | 1/2019 | Ohba | B01D 15/00 |

FOREIGN PATENT DOCUMENTS

| | | | | |
|---|---|---|---|---|
| EP | 3397386 A1 | * | 11/2018 | ............. B01D 15/00 |
| EP | 3397385 B1 | * | 6/2021 | ........... B01D 15/362 |
| JP | H01-228560 A | | 9/1989 | |
| JP | H01228560 A | * | 9/1989 | ............. G03F 7/004 |
| JP | H07-208166 A | | 8/1995 | |
| JP | 2001-246377 A | | 9/2001 | |
| JP | 2009057286 A | | 1/2009 | |
| JP | 2009155208 A | * | 7/2009 | ............. B01J 41/04 |
| JP | 5096907 B2 | | 12/2012 | |
| JP | 2013023441 A | | 1/2013 | |
| JP | 2013-023442 A | | 2/2013 | |
| WO | 2001/094284 A2 | | 12/2001 | |
| WO | 2003020393 A1 | | 3/2003 | |

(Continued)

OTHER PUBLICATIONS

Mitsubishi, Diaion® PK228 Product Data and Diaion® PA316 Product Data, Feb. 1, 2001, accessed on the Internet at https://www.lenntech.com/products/resins/mitsubishin-resins.htm, Sep. 29, 2019, (Year: 2001).*

Amberlyst 15, Amberlyst 15 Product Data, Aug. 14, 2012, accessed on the Internet at https://www.lenntech.com/Data-sheets/Amberlyst-15wet-L.pdf, Jun. 18, 2021, 3 pages. (Year: 2012).*

Diaion PK228, Diaion PK228 Product Data, Feb. 1, 2001, accessed on the Internet at https://www.lenntech.com/products/resins/mitsubishin-resins.htm, Sep. 29, 2019, 2 pages. (Year: 2001).*

Diaion CR20, Diaion CR20 Product Data, Jan. 31, 2001, Accessed on the Internet at https://www.lenntech.com/Data-sheets/Mitsubishi-CR20-L.pdf, on Jun. 16, 2021, 2 pages. (Year: 2001).*

Diaion PA316, DiaionTM PA316 Product Data, Feb. 1, 2001, accessed on the Internet at https://www.lenntech.com/products/resins/mitsubishin-resins.htm, Sep. 29, 2019, 2 pages. (Year: 2001).*

(Continued)

*Primary Examiner* — Bobby Ramdhanie
*Assistant Examiner* — Denise R. Anderson

(57) ABSTRACT

Methods for the removal of ionic contaminants from a hydrophilic organic solvent by a mixed bed of ion exchange resins are described. A mixed bed of ion exchange resins with gel-type strong-acid cationic ion exchange resin with a specific moisture holding capacity and gel-type anionic ion exchange resin is used in some embodiments of such methods.

8 Claims, No Drawings

(56) References Cited

FOREIGN PATENT DOCUMENTS

| WO | WO03020393 A1 | * | 3/2003 | ............... B01J 39/05 |
| WO | WO-2017116755 A1 | * | 7/2017 | ........... B01D 15/362 |
| WO | WO-2017116759 A1 | * | 7/2017 | ............. B01D 15/00 |

OTHER PUBLICATIONS

"WO-2017116755-A1 Search Reports," WO-2017116755-A1 Common Citation Document (CCD) services website (https://ccd.fiveipoffices.org/CCD-2.2.1/), ISR (dated Jul. 6, 2017), WOISA (dated Jul. 6, 2017), and EPO supplemental report (dated Apr. 24, 2020, EP-3397385-A1, now patent EP-3397385-B1), 22 pages. (Year: 2022).*

"WO-2017116759-A1 Search Reports," WO-2017116759-A1 Common Citation Document (CCD) services website (https://ccd.fiveipoffices.org/CCD-2.2.1/), ISR (dated Feb. 21, 2017), WOISA (dated Feb. 21, 2017), and EPO supplemental report (dated Jul. 9, 2019, EP-3397386-A1), 18 pages. (Year: 2022).*

Dowex Datasheet, "Dowex Monosphere MR-450 UPW," Apr. 1, 2002, accessed on the Internet at https://www.lenntech.com/Data-sheets/Dowex-Monosphere-MR-450-UPW-L.pdf, Feb. 7, 2022, 2 pages. (Year: 2002).*

Amberjet Datasheet, "Amberjet(TM) UP6040 Semi-Conductor Grade Final Polishing Mixed Bed Resin," Apr. 7, 2007, accessed at https://www.lenntech.com/Data-sheets/Rohm-&-Haas-Amberjet-UP-6040-L.pdf, Feb. 7, 2022, 2 pages. (Year: 2007).*

PCT/US2016/067172, International Search Report and Written Opinion dated May 29, 2017.

PCT/US2016/067172, International Preliminary Report on Patentability dated Jul. 12, 2018.

Dowex Monosphere MR-450 UPW, 2002.

Amberjet™ UP6040 Semi-Conductor Grade Final Polishing Mixed Bed Resin, 2007.

EP1845332.2, Examination Report dated Apr. 24, 2020.

\* cited by examiner

PURIFICATION PROCESS FOR HYDROPHILIC ORGANIC SOLVENT

FIELD

The present invention relates generally to methods for removal of contaminants from hydrophilic organic solvent. In particular, the present invention relates to methods for removal of metallic and non-metallic ionic contaminants from hydrophilic organic solvent using a mixed bed of ion exchange resins.

INTRODUCTION

Pure solvent, free of ionic contaminants, is required for many industrial purposes such as for the manufacture of pharmaceuticals and electronic materials. In particular, hydrophilic organic solvents with a quite low level of metallic ion contaminants are required for semiconductor fabrication processes because contamination with metal ions negatively affects the performance of semiconductor devices. Some hydrophilic organic solvents are useful for semiconductor fabrication processes including, for example, alcohols and ethers such as propylene glycol methyl ether (PGME). Therefore, when hydrophilic organic solvents are used in semiconductor fabrication processes, it would be desirable for such solvent to have a quite low level of metallic ion contaminants.

Ion exchange resins have been used for purification of water by removing ionic contaminants from water. Recently, such ion exchange technology has been applied to purification of organic solvents which are used in manufacturing electronic materials. However, it is believed that the behavior of ionic contaminants in organic solvent is different from their behavior in water because of the differences in polarities, such that the technology for purification of water using ion exchange resins is not generally expected to be suitable for use in the purification of organic solvent directly.

Previous methods for metal ion removal from organic solvents have been disclosed. U.S. Pat. No. 7,329,354 discloses a system for purification of an organic solvent by ion exchange resin. JP5,096,907B discloses a method for removal of anionic impurities from an ester by weak anionic exchange resin or anionic exchange resin in which OH groups in the anionic exchange resin are capped and inactivated. U.S. Pat. No. 6,123,850 discloses a method for purification of virtually anhydrous organic liquids by a cationic exchange resin based on a polystyrene-divinylbenzene copolymer with quite high contents (50-60%) of divinylbenzene. JP2009057286A discloses a method for removal cationic impurity from alcohol by cationic exchange resin with 8 wt % or less of crosslinkage. U.S. Pat. No. 5,518,628 discloses a method for removal of ionic contamination from an organic solution using a mixed bed ion exchange resin in which strong-base anionic exchange resin of the mixed bed ion exchange resin is modified by an ammonium salt of a weak organic acid.

However, these processes are insufficient for the removal of ionic contaminants from organic solvents to be used in applications requiring a quite high level of purity. Therefore, new processes for the removal of high levels of ionic contaminants from hydrophilic organic solvent are desired.

SUMMARY

The present invention provides processes for the removal of ionic contaminants from a hydrophilic organic solvent such that the solvent has a quite low level of ionic contaminants. In some embodiments, the process uses a mixed bed of ion exchange resins comprising a gel-type strong-acid cationic ion exchange resin with a specific moisture holding capacity (40-55 wt %) and a gel-type anionic ion exchange resin. In using the mixed bed of ion exchange resins, quite pure hydrophilic organic solvents with low metallic and nonmetallic ion contaminants can be obtained.

Therefore, one aspect of the invention relates to a method for removing ionic contaminations from a hydrophilic organic solvent that comprises contacting the hydrophilic organic solvent with a mixed bed of ion exchange resins comprising cationic ion exchange resins and anionic ion exchange resins, wherein (a) the cationic ion exchange resins are hydrogen (H) form strong-acid cationic ion exchange resins with a moisture holding capacity from 40 to 55 wt % and (b) both the cationic ion exchange resins and the anionic ion exchange resins have a porosity of 0.001 to 0.1 $cm^3/g$, an average pore size of 0.001 to 1.7 nm, and a B.E.T. surface area of 0.001 to 10 $m^2/g$.

Another aspect of the invention relates to a hydrophilic organic solvent obtained by the methods described herein, wherein the concentrations of Na, K, Ca, Al, Fe, Ni, Zn, Cu, Cr and Sn are each 0.1 ppb or less.

In another aspect, the invention relates to a method for removing ionic contaminants from a hydrophilic organic solvent, that comprises the steps of (i) preparing a mixed bed of ion exchange resins comprising cationic ion exchange resins and anionic ion exchange resins, wherein (a) the cationic ion exchange resins are hydrogen (H) form strong-acid cationic ion exchange resins with a moisture holding capacity from 40 to 55 wt % and (b) both the cationic ion exchange resins and the anionic ion exchange resins have a porosity of 0.001 to 0.1 $cm^3/g$, an average pore size of 0.001 to 1.7 nm, and a B.E.T. surface area of 0.001 to 10 $m^2/g$, and (ii) contacting a hydrophilic organic solvent with the mixed bed of ion exchange resins.

DETAILED DESCRIPTION

As used throughout this specification, the abbreviations given below have the following meanings, unless the context clearly indicates otherwise: g=gram(s); mg=milligram(s); L=liter(s); mL=milliliter(s); ppm=parts per million; ppb=parts per billion; m=meter(s); mm=millimeter(s); cm=centimeter(s); min=minute(s); s=second(s); hr.=hour(s); ° C.=degree(s) C.=degree(s) Celsius; vol %=volume percent(s); wt %=weight percent(s).

Methods of the present invention are generally applicable to hydrophilic organic solvents. In particular, methods are useful for water miscible protic solvents such as hydrophilic organic solvents. Examples of hydrophilic organic solvents include, but are not limited to, alcohols, ethers and mixtures thereof. Examples of alcohols for which methods of the present invention can be used include methanol, ethanol, propanol, propanol, and mixtures thereof. Examples of ethers for which methods of the present invention can be used include propylene glycol mono-methyl ether (PGME), dipropylene glycol mono-methy ether, diethylene glycol mono ethyl ether, diethylene glycol mono-butyl ether, and mixtures thereof.

Methods of the present invention use a mixed bed of ion exchange resins. A mixed bed of ion exchange resins refers to a mixture of cationic ion exchange resins and anionic ion exchange resins. The cationic ion exchange resins used in the mixed bed of ion exchange resins are hydrogen (H)-form strong-acid cationic ion exchange resins, which include cation exchange groups attached to polymer molecules which form resin beads. Examples of such H-form strong acid cation exchange groups include sulfonic acids. A H-form strong acid cation exchange group, such as a sulfonic acid, easily releases a proton ($H^+$) in exchange with a cationic impurity in the hydrophilic organic solvent. The resin beads of the cationic exchange resins are a polymer with normally spherical shape formed from a composition comprising styrene and divinylbenzene. Thus, in some embodiments, a H-form strong acid cationic exchange resin comprises sulfonic acid attached to polymer molecules formed from a composition comprising styrene and divinylbenzene.

The moisture holding capacity of the cationic ion exchange resins used in the mixed bed of ion exchange resins is from 40 to 55 wt %. The moisture holding capacity refers an amount of water in an ion exchange resin when the ion exchange resin is in a hydrated state (swelled in water). The moisture holding capacity varies with many factors, principally a chemical structure of the base resin (styrene-type or acrylic-type), degrees of crosslink of base resin, morphological type of base resin bead (gel-type or MR-type) and, size of ion exchange resin beads, population of cation exchange groups. In some preferred embodiments, the moisture holding capacity of the cationic ion exchange resins is from 45 to 50 wt % in a hydrated state. As used herein, the moisture holding capacity is calculated by the following method: a content of water in the cationic ion exchange resins is calculated by comparison of the weights of ion exchange resin before and after drying. The drying condition is at 105° C. for 15 hours under a 20 mmHg vacuum, followed by cooling in desiccators for 2 hours. The degreased weight after drying based on a hydrated state ion exchange resin is used to determine the moisture holding capacity based on the following formula:

Moisture Holding Capacity=(Weight of Hydrated Ion Exchange Resin−Weight of Ion Exchange Resin after Drying)*100/Weight of Hydrated Ion Exchange Resin An anionic ion exchange resin used in the mixed bed of ion exchange resins is preferably a strong-base anionic ion exchange resin. The anionic ion exchange resin has anion exchange groups attached to resin beads. In some embodiments, the strong-base anionic ion exchange resin comprises trimethyl ammonium groups (called Type I) or dimethyl ethanol ammonium groups (Type II) attached to polymer molecules which form anionic ion exchange resin beads. The strong-base anionic ion exchange resin releases hydroxyl ions ($OH^-$) in exchange with anionic contaminants in a hydrophilic organic solvent. The resin beads of the anionic ion exchange resins are also a polymer with normally spherical shape formed from a composition comprising styrene and divinylbenzene. Thus, in some embodiments, a strong base anionic exchange resin comprises trimethyl ammonium and/or dimethyl ethanol ammonium groups on a resin bead formed from a composition comprising styrene and divinylbenzene. Although the moisture holding capacity of the anionic ion exchange resins are not particularly limited, the moisture holding capacity is from 55 to 65 wt % when measured as described above, in some preferred embodiments.

The inventors of the present invention have found that a mixed bed of ion exchange resins as described herein can remove metals more effectively as compared to a cation single bed, and that such mixed beds of ion exchange resins incorporating a specific cationic ion exchange resin (i.e., H-type strong acid cationic ion exchange resins with moisture holding capacity from 40 to 55 wt %) can provide a quite pure hydrophilic organic solvent with less ionic contaminants.

As mentioned above, a H-form strong acid cation exchange group releases a proton ($H^+$) in exchange with a cationic impurity in a hydrophilic organic solvent. The inventors of the present invention found that a H-form strong acid cationic ion exchange resin with moisture holding capacity from 40 to 55 wt % has the highest ion exchange ability in a hydrophilic organic solvent. When an ion exchange resin is swelled in an organic solvent, a larger amount of hydrophilic solvent can permeate into the interior of the resin bead because of less steric hindrance. As a result, the frequency of ion exchange reaction increases as ion exchange groups located inside the bead can also contribute to ion exchange reaction. In contrast, a denser state resin allows less permeation of the solvent, and only superficial ion exchange sites located on the surface of resin beads contribute to ion exchange reaction. On the other hand, the strong-base anionic ion exchange resins used in the mix bed release hydroxyl ions ($OH^-$) in exchange with anionic impurities. The released protons and hydroxyl ions form water ($H_2O$) in a hydrophilic organic solvent. Because a hydrophilic organic solvent has a strong affinity with water, the formed water is mixed with the hydrophilic organic solvent such that the water is removed from the vicinity of the mixed bed of ion exchange resins. In the presence of protons, a cation exchange reaction will not proceed according to the theory of equilibrium reaction. By using the mix bed of strong acid cation exchange resins and strong base anion exchanges, protons are more effectively removed as water such that more ionic impurities are bonded with ion exchange resins in the mixed bed of ion exchange resin.

Both the cationic ion exchange resins and anionic ion exchange resins are gel-type resins in embodiments of the present invention. As used herein, and as generally understood in the field of ion exchange resins, a gel-type resin refers to a resin that has a very low porosity (less than 0.1 $cm^3/g$), a small average pore size (less than 1.7 nm) and a low B.E.T. surface area (less than 10 $m^2/g$). Porosity, average pore size and B.E.T. surface area can be measured by the nitrogen adsorption method shown in ISO 15901-2. Such ion exchange resins are distinct from macroporous-type ion exchange resins having a macro-reticular structure (MR-type ion exchange resin) and a macro pore size that is clearly larger than the porosity of gel-type ion exchange resins.

Gel-type ion exchange resins are preferred for use in the present invention for a few reasons: (1) a gel-type ion exchange resin is easily swelled by hydrophilic organic solvent because it has less cross-linking than typical commercially available macroporous or macro-reticular (MR) type ion exchange resins which are designed for high stability of morphology; and (2) ionic impurities contained in gel-type ion exchange resins are generally lower than ionic impurities contained in MR-type ion exchange resins. The ionic exchange resins used in the mixed bed of ionic exchange resins, the resins preferably have a moisture holding capacity of 40 to 55 weight percent. For resins with high moisture holding capacity (e.g., greater than 55 wt %), there is a higher risk of organics leaching from the ion exchange resin. For resins with lower moisture holding capacity (e.g., less than 40 wt %), it is difficult to rinse down contaminants from the ion exchange resin using a typical rinse procedure, and the activity of the ion exchange groups is low due to high stereo hindrance in the hydrophilic organic solvent.

The ratio of cationic ion exchange resin to anionic ion exchange resin in the mixed bed of ion exchange resins is generally from 1:9 to 9:1 in equivalence ratio of ion exchange groups, in some embodiments. Preferably, the ratio is from 2:8 to 8:2.

Sometimes cationic ion exchange resins and/or anionic ion exchange resins contain metal impurities originating from its manufacturing process. Such metal impurities might come out from the resins and cause metal ion contamination in the processed solvent. Without wishing to be bound to any particular theory, the inventors believe that such leaching metal impurities combine with low-molecular weight organic compounds which are contained in the ion exchange resins as a side-reaction product or unreacted/un cross-linked product of resins. Such a metal-organic compound complex is more easily dissolved in an organic solvent such that the organic compound carries the metal impurity into an organic solvent. Therefore, the inventors believe that it is desirable to minimize the amount of metal impurities and/or leachable species of low molecular weight organic compounds in the ion exchange resins to decrease the potential for ion contamination in the solvent to be processed.

Metal impurities contained in ion exchange resins can include Na, K, Ca, Al, Fe, Ni, Zn, Cu, Sn and Cr. To prevent metal ion contamination from ion exchange resins, the contents of these individual metal impurities in ion exchange resins to be used in some embodiments of the present invention are preferably 10 mg/Kg or less respectively, based on the dry-weight of the ion exchange resins. More preferably, the contents of these metal ions are 5 mg/Kg or less based on the dry-weight of the ion exchange resins. The contents of the metals can be analyzed with ICP-MS after resin sample ashing (i.e. burning the ion exchange resins, dissolving the remained ash to hydrochloric acid aqueous solution, and analyzing the concentrations of metal ions by ICP-MS).

The contents of leachable species of low-molecular organic compounds included in ion exchange resins can be evaluated by the following method. Firstly, ultra pure water is flown continuously into an ion exchange resin column at 25 BV/hr, then TOC (total organic carbon) values of inlet ultra pure water (called UPW) and outlet UPW are measured after 24 hours flow. Then, the difference, or delta ($\Delta$) TOC value, is calculated from the two TOC values. $\Delta$ TOC value is calculated by subtraction of the inlet TOC value from the outlet TOC value. In some embodiments of the present invention, the $\Delta$ TOC value measured by the above method is preferably 10 ppb or less. More preferably, $\Delta$ TOC value is 5 ppb or less. TOC can be analyzed by commercially available TOC analysers using techniques known to those in the skill in the art.

The cationic ion exchange resin and anionic ion exchange resin originally contain water (swelled by water in equilibrium condition with water). In this invention, contents of water in the cationic ion exchange resin and anionic ion exchange resin are decreased to 5 wt % or less respectively (i.e. for each resin) prior to use. Preferably, the contents of water in cationic ion exchange resin and anionic ion exchange resin are 3 wt % or less in each resin. Starting the resin bed with dry resin can save the solvation time of ion exchange resin, and also, it can minimize the solvent volume that is required to displace water. To decrease the content of water, cationic ion exchange resin and anionic ion exchange resin can be dried before contacting with a hydrolysable organic solvent. An apparatus of drying and conditions such as temperature, time and pressure for drying ion exchange resins can be selected using techniques known to those of skill in the art. For example, the ion exchange resins can be heated in an oven at 60 to 120° C. for 1 to 48 hours under decompressed condition. The content of water can be calculated by comparison of the weights of ion exchange resin before and after heating it at 105° C. for 15 hours in a lower than 20-mmHg vacuum oven, followed by cooling down in a desiccator for 2 hours.

When contacting a hydrophilic organic solvent with a mixed bed of ion exchange resin, any known methods for contacting liquids with ion exchange resins can be used. For example, a mixed bed ion exchange resin can be packed in a column and the solvent can be poured from the top of the column through the mixed bed ion exchange resin. The flow rate of the solvent can be from 1 to 100 BV/hr, preferably from 1 to 50 BV/hr. As used herein, "BV" means bed volume, and refers to an amount of liquid contacted with the same volume of a hydrated wet mixed bed ion exchange resin. For example, if 120 ml of a hydrated wet mixed bed ion exchange resin is used, 1 BV means 120 ml of hydrophilic organic solvent is contacted with the mixed bed ion exchange resin. 'BV/hr' was calculated by flow rate (mL/hr) divided by bed volume (mL).

The temperature during contacting a hydrophilic organic solvent with a mixed bed ion exchange resin can be from 0 to 100° C., preferably from 10 to 60° C., more preferably from 20 to 40° C., in various embodiments.

The obtained hydrophilic organic solvent includes quite low-level of metallic and non-metallic ionic contaminations. The contaminations can include Na, K, Ca, Al, Fe, Ni, Zn, Cu, Sn and Cr. The concentrations of these contaminations can be 0.1 ppb or less respectively, in various embodiments. Therefore, hydrophilic organic solvents obtained using methods of the present invention can be useful in applications which requires a quite high level of pure solvent, such as for the manufacture of pharmaceuticals and electronic materials, and especially for use in semiconductor fabrication process.

Some embodiments of the invention will now be described in detail in the following Examples.

EXAMPLES

The following ion exchange resins were used.
Mixed Ion Exchange Resin

|  | AMBERLITE ™UP6040 | |
| --- | --- | --- |
|  | Strong cation exchange | Strong anion exchange |
| Resin type | Gel | Gel |
| Moisture holding capacity (wt %) | 46-51 | 54-60 |

Cationic Ion Exchange Resin

|  | DOWEX ™ MONOSPHERE 650C UPW Strong cation exchange | DOWEX ™ MAC-3 Weak cation exchange | AMBERLYST ™ 31Wet Strong cation exchange | AMBERLYST ™ 15Wet Strong cation exchange |
| --- | --- | --- | --- | --- |
| Resin type | Gel | Gel | Gel | Macro-reticular (MR) |

|  | DOWEX™ MONOSPHERE 650C UPW Strong cation exchange | DOWEX™ MAC-3 Weak cation exchange | AMBERLYST™ 31Wet Strong cation exchange | AMBERLYST™ 15Wet Strong cation exchange |
| --- | --- | --- | --- | --- |
| Moisture Holding capacity (wt %) | 46-51 | 44-52 | 63-67 | 51-56 |

Anionic Ion Exchange Resin

|  | AMBERJET™ UP4000 Strong anion exchange | AMBERJET™ 9000_OH Strong anion exchange | AMBERLITE™ IRA9O4_Cl Strong anion exchnage |
| --- | --- | --- | --- |
| Resin type | Gel | MR | MR |
| Moisture Holding capacity (wt %) | 54-60 | 66-75 | 57-63 |

Comparative Example 1

Strong Cation Exchange Resin DOWEX™ MONOSPHERE™ 650 C UPW 120 mL (94 g) of hydrated state DOWEX™ MONOSPHERE™ 650 C UPW (MS650C UPW, Gel type strong cation exchange resin) is charged to a Teflon column with 20 mm for internal diameter and 500 mm for length. DOWANOL™ PM (PM) is flowed at 40 mL/min for 3 hours for water displacement with PM. Then sampling is started, varying the flow rate.

Comparative Example 2

Strong Cation Exchange Resin Bed MS650C UPW is Rinsed with PM Flow

After conducting "Comparative example 1" test, the flow rate is reduced and continued to feed PM at 2 BV/hr. After 48 hr flow at 2 BV/hr, the flow rate is increased to 16 BV/hr and samples are taken.

Resin volume shrinks to approximately 100 mL in PM-solvated state for comparative examples 1 and 2.

Comparative Example 3

Weak Cation Exchange Resin DOWEX™ MAC-3

Hydrated state MAC-3 resin (Gel type weak cation exchange resin) is charged to the TEFLON column with 20 mm for internal diameter and 500 mm for length. After water is displaced with PM flow for 3 hours at 16 BV/hr, the first PM sample is taken. Resin volume expands to 150 mL in PM-solvated state from 120 ml in hydrated state.

Comparative Example 4

Dry Mix Bed of Strong Cation Exchange Resin with High Moisture Holding Capacity and MR-Type Strong Anion Resin 40 ml of hydrated state AMBERLYST™ 31WET (Gel type strong cationic exchange resin) and 80 ml of hydrated state AMBERJET™ 9000 OH (MR type strong anion exchange resin) is mixed. ΔTOC is measured as 12.8 ppb after 2-hour UPW flow at 25 BV/hr and 2.3 ppb after 24-hour flow.

The mix resin is dried in vacuum oven (60° C., 20 mmHg, 15 hr). After 2 hr flow of PM at 16 BV/hr flow rate, the first sample is taken. Then, other samples are taken, varying the flow rate. 120 mL of the hydrated resin volume shrinks to 96 mL in PM Solvated state.

Comparative Example 5

Mix Bed of MR Type Strong Cation Exchange Resin and MR Type Strong Anion Resin

AMBERLITE 904Cl (MR type Cl⁻ form Strong cation exchange resin) is converted to OH form by the following manner.

500 mL of AMBERLITE™ 904 Cl is charged to a stainless steel column with 50 mm for diameter and 800 mm for length. 4 wt % cautic soda aqueous solution is heated in 60 deg. C. temperature controlled tank. Heated 4% cautic soda solution is flowed from top of the column at 10 BV/hr for 2 hours to convert chlorine form to hydroxyl form. Then, UPW flow rinse is made at 10 BV/hr for 2 hr at room temperature. The resin taken from the column is hydrated state OH-converted anion exchange resin.

A mixed bed is constructed in the following manner.

40 ml of hydrated AMBERLYST™ 15WET (MR type H form Strong cation exchange resin) and 80 ml of the hydrated state OH-converted AMBERLITE™ 904 Cl are mixed uniformly. The above volume base mix ratio of the cation exchange resin and the anion exchange resin is 1:1 in equivalent ratio. ΔTOC of the hydrated state mix resin is measured as 98 ppb after 2-hour UPW flow at 25 BV/hr flow rate and 30 ppb after 24-hour flow.

The mixed resin is dried in vacuum oven (60° C., 20 mmHg) for 15 hrs The dried mix resin is charged to a Teflon column with 20 mm for inner diameter and 500 mm for length. PM is flowed at 16 BV/hr flow rate for 2 hours. 120 mL of hydrated resin volume shrinks to 108 mL in PM solvated state. Samples are taken, varying the flow rate.

Example 1

Mix Bed of Strong Cation Exchange Resin MS650C UPW and Strong Anion Exchange Resin AMBERJET™ UP4000

Hydrated wet cation resin MS650 C UPW and hydrated wet anion resin AMBERJET™ UP4000 are mixed at the weight ratio of 39:61 as 1:1 for equivalent weight ratio. ΔTOC was measured as 8.2 ppb after 2-hour UPW flow at 25 BV/hr and 0.7 ppb after 24-hour UPW flow. Dry resin-base metal contents in the mix resin are measured as 0.13 mg/Kg for Na, 0.12 mg/Kg for Al, 0.17 mg/Kg for Ca, 1.44 mg/Kg for Fe, 0.01 mg/Kg for Cu.

120 mL of the mix resin is loaded into the Teflon column with 20 mm for inner diameter and 500 mm for length.

PM is flowed at 16 BV/hr for 3 hours to displace water with PM, followed by flow stop for a night. The resin volume shrinks from 120 mL in hydrated state to 114 mL in PM-solvated state. Then, the first sample is taken after 1 hr flow at 16 BV/hr in the next day. Other samples are taken, changing the flow rate.

Example 2

Mix Resin AMBERLITE™ UP6040 (Dry Resin)

ΔTOC of the tested resin is measured as 1.9 ppb after 2-hour UPW flow at 25 BV/hr and less than 0.1 ppb after 24-hour UPW flow.

120 ml of hydrated state AMBERLITE™ UP6040 (1:1: stoichometrical mixture of Strong cation exchange resin and weak anion exchange resin) is dried in 105° C. at 20 mmHg for 15 hours. Dry resin base metal contents in the mix resin are measured as 0.18 mg/Kg for Na, 0.12 mg/Kg for Al, 0.18 mg/Kg for Ca, 3.42 mg/Kg for Fe, 0.00 mg/Kg for Cu and 0.02 mg/Kg for Zn.

The dried resin is charged to Teflon column and PM is flowed for 3 hours at 16 BV/hr for solvation purpose, and stop the flow for a night. The resin volume expands to 131 mL in PM-solvated state from 125 mL of hydrated state.

The first samples are taken after 1 hour flow at 16 BV/hr in the next day. Other samples are taken, changing the flow rate.

Analysis

The concentrations of metals in the solvent samples are analyzed by ICP-MS (Inductively Coupled Plasma-mass spectrometry), and the analytical results are shown in Tables 1 to 6. Original metal level (concentration) and metal element ratio are varied by feed solvent lot.

The concentration of 1-methoxy-2-propanol (a main component in PM) is evaluated with GC-FID (Gas chromatography-flame ionization detector) and the results are shown in Tables 1 to 6. Definition of purity is area % of 1-methoxy-2 propanol.

TABLE 1

Evaluation results (Comparative Examples 1 to 2)

| | Comparative Example 1 MS650C UPW | | | | Comparative Example 2 MS650C UPW | |
|---|---|---|---|---|---|---|
| | Metal (ppb) in DOWANOL ™ PM | | | | | |
| | Original | 32 BV/Hr | 16 BV/Hr | 8 BV/Hr | Original | 16 BV/Hr |
| Na | 2.48 | 1.00 | 0.77 | 1.28 | 2.98 | 0.23 |
| Fe | 1.27 | 0.07 | 0.07 | 0.11 | 0.94 | 0.10 |
| K | 0.73 | 0.10 | 0.18 | 0.28 | 0.53 | 0.19 |
| Ca | 0.06 | 0.05 | 0.16 | 0.44 | 0.10 | 0.17 |
| Cu | 0.05 | 0.05 | 0.07 | 0.09 | 0.01 | 0.01 |
| Mg | 0.32 | 0.15 | 0.20 | 0.30 | 0.10 | 0.04 |
| Mn | 0.02 | 0.01 | 0.02 | 0.02 | 0.01 | 0.01 |
| Al | 0.07 | 0.14 | 0.07 | 0.08 | 1.43 | 0.09 |
| Cr | 0.11 | 0.04 | 0.04 | 0.05 | 0.72 | 0.17 |
| Ni | 0.05 | 0.03 | 0.03 | 0.06 | 0.03 | 0.02 |
| Pb | 0.00 | 0.00 | 0.00 | 0.01 | 0.00 | 0.00 |
| Zn | 0.33 | 0.10 | 0.14 | 0.36 | 0.23 | 0.13 |
| Li | 0.01 | 0.01 | 0.01 | 0.01 | 0.03 | 0.03 |
| Sn | 0.18 | 0.32 | 0.08 | 0.08 | 0.05 | 0.02 |
| Sum of 14metals | 5.69 | 2.08 | 1.84 | 3.16 | 7.16 | 1.19 |
| Residual metal (%) | | 37 | 32 | 56 | | 17 |
| Purity(%) | 99.91 | 99.91 | — | 99.90 | 99.99 | 99.97 |

TABLE 2

Evaluation results (Comparative Examples 3)

| | Comparative Example 3 MAC-3 | | |
|---|---|---|---|
| | Metal (ppb) in DOWANOL ™ PM | | |
| | Original | 16 BV/Hr | 4 BV/Hr |
| Na | 5.66 | 5.38 | 5.45 |
| Fe | 0.49 | 0.42 | 0.39 |
| K | 0.51 | 0.32 | 0.34 |
| Ca | 0.91 | 0.32 | 0.52 |
| Cu | 0.02 | 0.01 | 0.02 |
| Mg | 0.18 | 0.05 | 0.18 |
| Mn | 0.02 | 0.01 | 0.02 |
| Al | 0.00 | 0.02 | 0.02 |
| Cr | 6.96 | 6.32 | 7.22 |
| Ni | 0.02 | 0.01 | 0.02 |
| Pb | 0.01 | 0.00 | 0.01 |
| Zn | 1.10 | 0.12 | 1.60 |
| Li | 0.00 | 0.00 | 0.00 |
| Sn | 0.06 | 0.04 | 0.06 |
| Sum of 14metals | 15.94 | 13.02 | 15.86 |
| Residual metal (%) | | 82 | 100 |
| Purity(%) | 99.81 | 99.73 | 99.73 |

TABLE 3

Evaluation results (Comparative Examples 4)

| | Comparative Example 4 Dry mix of AMBERLYST ™ 31 Wet/ AMBERJET ™ 9000 OH | | | |
|---|---|---|---|---|
| | Metal (ppb) in DOWANOL ™ PM | | | |
| | Original | 32 BV/Hr | 16 BV/Hr | 8 BV/Hr |
| Na | 4.21 | 5.33 | 1.55 | 0.94 |
| Fe | 0.33 | 0.12 | 0.24 | 0.13 |
| K | 0.05 | 0.02 | 0.02 | 0.02 |
| Ca | 0.20 | 0.21 | 0.13 | 0.15 |
| Cu | 0.08 | 0.00 | 0.00 | 0.00 |
| Mg | 0.07 | 0.00 | 0.01 | 0.00 |
| Mn | 0.02 | 0.00 | 0.00 | 0.00 |

TABLE 3-continued

Evaluation results (Comparative Examples 4)

Comparative Example 4
Dry mix of AMBERLYST ™ 31 Wet/
AMBERJET ™ 9000 OH
Metal (ppb) in DOWANOL ™ PM

|  | Original | 32 BV/Hr | 16 BV/Hr | 8 BV/Hr |
|---|---|---|---|---|
| Al | 0.04 | 0.00 | 0.01 | 0.01 |
| Cr | 2.48 | 0.09 | 0.07 | 0.04 |
| Ni | 0.02 | 0.00 | 0.00 | 0.00 |
| Pb | 0.00 | 0.00 | 0.00 | 0.00 |
| Zn | 0.34 | 0.00 | 0.00 | 0.00 |
| Li | 0.01 | 0.00 | 0.00 | 0.00 |
| Sn | 0.26 | 0.05 | 0.05 | 0.02 |
| Sum of 14metals | 8.11 | 5.82 | 2.07 | 1.31 |
| Residual metal (%) |  | 72 | 26 | 16 |
| Purity (%) | 99.89 | — | — | 99.89 |
| ΔTOC 2 hr |  | 12.8 ppb | | |
| 24 hr |  | 2.3 ppb | | |

TABLE 4

Evaluation results (Comparative Examples 5)

Comparative Example 5
Dry mix of AMBERLYST ™ 15WET/
AMBERLITE ™ IRA904
Metal (ppb) in DOWANOL ™ PM

|  | Original | 32 BV/Hr | 16 BV/Hr | 8 BV/Hr |
|---|---|---|---|---|
| Na | 5.70 | 1.99 | 0.83 | 0.68 |
| Fe | 1.06 | 0.08 | 0.14 | 0.10 |
| K | 0.34 | 0.34 | 0.14 | 0.12 |
| Ca | 1.70 | 0.77 | 0.53 | 1.14 |
| Cu | 0.07 | 0.01 | 0.01 | 0.01 |
| Mg | 0.10 | 0.07 | 0.04 | 0.03 |
| Mn | 0.02 | 0.00 | 0.00 | 0.00 |
| Al | 0.21 | 0.14 | 0.18 | 0.17 |
| Cr | 2.63 | 0.37 | 0.17 | 0.15 |
| Ni | 0.02 | 0.01 | 0.00 | 0.00 |
| Pb | 0.00 | 0.00 | 0.00 | 0.00 |
| Zn | 0.31 | 0.05 | 0.02 | 0.02 |
| Li | 0.00 | 0.00 | 0.00 | 0.00 |
| Sn | 0.38 | 0.06 | 0.03 | 0.06 |
| Sum of 14metals | 12.55 | 3.89 | 2.11 | 2.49 |
| Residual metal (%) |  | 31 | 17 | 20 |
| Purity (%) | 99.89 | — | — | 99.89 |
| ΔTOC 2 hr |  | 98 ppb | | |
| 24 hr |  | 30 ppb | | |

TABLE 5

Evaluation results (Inventive Example 1)

Example 1
MS650/UP4000 (Hydrated state)
Metals (ppb) in DOWANOL ™ PM

|  | Original | 32 BV/Hr | 16 BV/Hr | 8 BV/Hr |
|---|---|---|---|---|
| Na | 2.21 | 0.05 | 0.05 | 0.04 |
| Fe | 2.99 | 0.48 | 0.32 | 0.12 |
| K | 0.08 | 0.06 | 0.05 | 0.02 |
| Ca | 0.41 | 0.04 | 0.03 | 0.05 |
| Cu | 0.01 | 0.00 | 0.00 | 0.00 |
| Mg | 0.22 | 0.05 | 0.02 | 0.01 |
| Mn | 0.02 | 0.00 | 0.00 | 0.00 |
| Al | 0.02 | 0.01 | 0.01 | 0.00 |
| Cr | 0.27 | 0.05 | 0.02 | 0.01 |
| Ni | 0.03 | 0.01 | 0.01 | 0.01 |
| Pb | 0.00 | 0.00 | 0.00 | 0.00 |
| Zn | 0.43 | 0.06 | 0.02 | 0.01 |
| Li | 0.00 | 0.00 | 0.00 | 0.00 |
| Sn | 0.01 | 0.00 | 0.00 | 0.00 |
| Sum of 14 metlas | 6.71 | 0.83 | 0.55 | 0.26 |
| Residual metal (%) |  | 12 | 8 | 4 |
| Purity (%) | 99.90 | — | 99.90 | — |
| ΔTOC (2 hr) |  | 8.2 ppb | | |
| (24 hr) |  | 0.7 ppb | | |

TABLE 6

Evaluation results (Inventive Example 2)

Example 2
AMBERLITE ™ UP6040 (Dried)
Metals (ppb) in DOWANOL ™ PM

|  | Original | 32 BV/Hr | 16 BV/Hr | 8 BV/Hr |
|---|---|---|---|---|
| Na | 6.03 | 0.05 | 0.38 | 0.09 |
| Fe | 1.36 | 0.17 | 0.07 | 0.06 |
| K | 0.13 | 0.02 | 0.03 | 0.04 |
| Ca | 0.25 | 0.03 | 0.08 | 0.02 |
| Cu | 0.02 | 0.01 | 0.01 | 0.00 |
| Mg | 0.19 | 0.02 | 0.06 | 0.01 |
| Mn | 0.01 | 0.00 | 0.00 | 0.00 |
| Al | 0.05 | 0.03 | 0.04 | 0.03 |
| Cr | 0.15 | 0.02 | 0.02 | 0.01 |
| Ni | 0.01 | 0.01 | 0.01 | 0.01 |
| Pb | 0.00 | 0.00 | 0.00 | 0.00 |
| Zn | 0.74 | 0.03 | 0.02 | 0.01 |
| Li | 0.00 | 0.00 | 0.00 | 0.00 |
| Sn | 0.04 | 0.01 | 0.00 | 0.04 |
| Sum of 14 metlas | 9.00 | 0.41 | 0.71 | 0.32 |
| Residual metal (%) |  | 5 | 8 | 4 |
| Purity (%) | 99.91 | — | — | 99.91 |
| ΔTOC 2 hr |  | 1.9 ppb | | |
| 24 hr |  | 0.0 ppb | | |

We claim:

1. A method for removing ionic contamination from a hydrophilic organic solvent, the method comprising:
   contacting the hydrophilic organic solvent with a mixed bed of ion exchange resins comprising cationic ion exchange resins and anionic ion exchange resins, wherein:
   (a) the cationic ion exchange resins are hydrogen (H) form strong-acid cationic ion exchange resins with a moisture holding capacity from 40 to 55 wt %, and
   (b) both the cationic ion exchange resins and the anionic ion exchange resins have a porosity of 0.001 to 0.1 cm$^3$/g, an average pore size of 0.001 to 1.7 nm, and a B.E.T. surface area of 0.001 to 10 m$^2$/g,
   wherein the hydrophilic organic solvent is a glycol ether or a mixture of glycol ethers and
   wherein the concentration of Na, K, Ca, Al, Fe, Ni, Zn, Cu, Cr and Sn in the hydrophilic organic solvent after contacting with the mixed bed of ion exchange resins is each 0.1 ppb or less.

2. The method of claim 1, wherein the mixed bed of ion exchange resins show 10 ppb or less of total organic carbon measured by the following method:

washing the mixed bed of ion exchange resins with 25 bed volumes (BV) of ultra pure water for 24 hours; and then analyzing total organic carbon of the ultra pure water.

3. The method of claim 1, wherein the contents of Na, K, Ca, Al, Fe, Ni, Zn, Cu, Cr and Sn in the H form strong cationic ion exchange resins and the anionic ion exchange resins are each 10 mg/kg or less based on dry weight of the ion exchange resins.

4. A hydrophilic organic solvent obtained by the method of claim 1, wherein the concentration of Na, K, Ca, Al, Fe, Ni, Zn, Cu, Cr and Sn in the hydrophilic organic solvent after contacting with the mixed bed of ion exchange resins is each 0.1 ppb or less.

5. The method of claim 1, wherein the hydrophilic organic solvent comprises propylene glycol mono-methyl ether, dipropylene glycol mono-methy ether, diethylene glycol mono ethyl ether, diethylene glycol mono-butyl ether, or a mixture thereof.

6. A method for removing ionic contamination from a hydrophilic organic solvent, comprising the steps of
(i.) preparing a mixed bed ion of exchange resins comprising hydrogen (H) form strong cationic ion exchange resins and strong anionic ion exchange resins, wherein:
   (a) the cationic ion exchange resins have a moisture holding capacity from 40 to 55 wt %, and
   (b) both the cationic ion exchange resins and the anionic ion exchange resins have a porosity of 0.001 to 0.1 cm$^3$/g, an average pore size of 0.001 to 1.7 nm, and a B.E.T. surface area of 0.001 to 10 m$^2$/g; and
(ii.) contacting a hydrophilic organic solvent with the mixed bed of ion exchange resins, wherein the hydrophilic organic solvent is a glycol ether or a mixture of glycol ethers and wherein the concentration of Na, K, Ca, Al, Fe, Ni, Zn, Cu, Cr and Sn in the hydrophilic organic solvent after contacting with the mixed bed of ion exchange resins is each 0.1 ppb or less.

7. The method of claim 6, wherein the method further comprises: (iii) rinsing the mixed bed of ion exchange resins by 30 to 50 bed volumes (BV) of the hydrophilic organic solvent under a flow rate of 1 to 50 BV/Hr, and step (iii) is conducted between steps (i) and (ii).

8. The method of claim 6, wherein the hydrophilic organic solvent comprises propylene glycol mono-methyl ether, dipropylene glycol mono-methy ether, diethylene glycol mono ethyl ether, diethylene glycol mono-butyl ether, or a mixture thereof.

* * * * *